US007264950B1

(12) United States Patent
Lee et al.

(10) Patent No.: US 7,264,950 B1
(45) Date of Patent: Sep. 4, 2007

(54) REACTION SYSTEM FOR PERFORMING IN THE AMPLIFICATION OF NUCLEIC ACIDS

(75) Inventors: Martin Alan Lee, Salisbury (GB); Hilary Bird, Salisbury (GB); Dario Lyall Leslie, Salisbury (GB); David James Squirrell, Salisbury (GB); John Shaw, Hayes (GB); David Wenn, Hayes (GB); Julie Deacon, Hayes (GB)

(73) Assignee: The Secretary of State for Defence in Her Britannic Majesty's Government of the United Kingdom of Great Britain and Northern Ireland, Salisbury, Wiltshire (GB)

(*) Notice: Subject to any disclaimer, the term of this patent is extended or adjusted under 35 U.S.C. 154(b) by 603 days.

(21) Appl. No.: 10/089,498

(22) PCT Filed: Sep. 29, 2000

(86) PCT No.: PCT/GB00/03743

§ 371 (c)(1),
(2), (4) Date: Mar. 28, 2002

(87) PCT Pub. No.: WO01/23093

PCT Pub. Date: Apr. 5, 2001

(30) Foreign Application Priority Data

Sep. 29, 1999 (GB) ................................ 9922971.8

(51) Int. Cl.
*C12P 19/34* (2006.01)
*C12Q 1/68* (2006.01)

(52) U.S. Cl. ......................... 435/91.2; 435/6; 435/91.1

(58) Field of Classification Search .................... 435/6, 435/91.1, 91.2; 536/23.1, 24.3, 24.33
See application file for complete search history.

(56) References Cited

U.S. PATENT DOCUMENTS 5,043,272 A * 8/1991 Hartley .......................... 435/5
5,075,216 A * 12/1991 Innis et al. .................... 435/6
5,234,811 A * 8/1993 Beutler et al. ................. 435/6
5,386,021 A * 1/1995 Moss et al. ................. 435/358
5,498,392 A 3/1996 Wilding et al.
5,501,963 A * 3/1996 Burckhardt ................ 435/91.2
5,512,462 A * 4/1996 Cheng ....................... 435/91.2
5,525,300 A * 6/1996 Danssaert et al. ............ 422/99
5,587,128 A * 12/1996 Wilding et al. ............... 422/50
5,766,890 A 6/1998 Kacian et al.
5,856,174 A 1/1999 Lipshutz et al.
5,944,971 A 8/1999 Foote
6,077,669 A * 6/2000 Little et al. .................... 435/6
6,238,869 B1 * 5/2001 Kris et al. ...................... 435/6
6,372,484 B1 * 4/2002 Ronchi et al. ........... 435/287.2
6,488,897 B2 * 12/2002 Dubrow et al. ............. 422/102

FOREIGN PATENT DOCUMENTS

WO WO89/10788 11/1989
WO WO9809728 A1 * 3/1998
WO WO98/24548 6/1998

OTHER PUBLICATIONS

Hertiz et al., "Detection of eubacteria in interstitial cystitis by 16 rDNA Amplification," The Journal of Urology, 1997, vol. 158, No. 6, pp. 2291-2295.*

* cited by examiner

*Primary Examiner*—Young J. Kim
(74) *Attorney, Agent, or Firm*—Kilpatrick Stockton LLP

(57) ABSTRACT

A method of carrying out an amplification reaction, said method comprising supplying to a well in a disposable unit (a) a sample which contains or is suspected of containing a target nucleic acid sequence (b) primers, nucleotides and enzymes required to effect said amplification reaction and (c) a buffer system, and subjecting the unit to thermal cycling conditions such that any target nucleic acid present within the sample is amplified; wherein the disposable unit comprises a thermally conducting layer and a facing layer having one or more reagent wells of up to 1000 microns in depth defined therebetween; and the reaction mixture comprises at least one of the following: A) a buffer system wherein the pH is above 8.3; B) a detergent; and/or C) a blocking agent. Apparatus for effecting the method as well as disposable units for use in the method are described. The method is particularly suitable for rapid PCR reactions.

26 Claims, 2 Drawing Sheets

REACTION SYSTEM FOR PERFORMING IN THE AMPLIFICATION OF NUCLEIC ACIDS

This application claims priority to Great Britain Application No. 9922971.8 filed on Sep. 29, 1999, which is incorporated herein by reference.

The present invention relates to a method of carrying out amplification reaction, in particular, the polymerase chain reaction (PCR) using a disposable unit, and to disposable units used in the method.

The controlled heating of reaction vessels in such methods is often carried out using solid block heaters which are heated and cooled by various methods. Current solid block heaters are heated by electrical elements or thermoelectric devices inter alia. Other reaction vessels may be heated by halogen bulb/turbulent air arrangements. The vessels may be cooled by thermoelectric devices, compressor refrigerator technologies, forced air or cooling fluids.

The reaction vessels, which are generally tubes or curvettes, fit into the block heater with a variety of levels of snugness. Thus, the thermal contact between the block heater and the reaction vessel varies from one design of heater to another. In reactions requiring multiple temperature stages, the temperature of the block heater can be adjusted using a programmable controller for example to allow thermal cycling to be carried out using the heaters.

A disadvantage of the known block heaters arises from the lag time required to allow the heating block to heat and cool to the temperatures required by the reaction. Thus, the time to complete each reaction cycle is partially determined by the thermal dynamics of the heater in addition to the rate of the reaction. For reactions involving numerous cycles and multiple temperature stages, this lag time significantly affects the time taken to complete the reaction. Thermal cyclers based on such block heaters typically take around 2 hours to complete 30 reaction cycles.

For many applications of the PCR technique it is desirable to complete the sequence of cycles in the minimum possible time. In particular for example where respiratory air or fluids or foods for human and animal stock consumption are suspected of contamination rapid diagnostic methods may save considerable money if not health, even lives.

Apparatus for thermally cycling a sample are described in WO98/09728. In this apparatus the reagents are held in a disposable unit which comprises a thin planar structure so as to ensure good thermal contact with reagents contained in the unit. The units are made either of plastics materials such as polycarbonate or polypropylene, or silicon. Silicon is preferred as the thermal conductivity ensures that the reagents are heated quickly. However in order to effect a PCR reaction, where biological reagents are employed, the silicon must be coated with a biocompatible layer.

Other forms of disposable unit are described for example in EP 0723812. These include units with metal elements such as aluminium. Although such units have good thermal properties, the fact that biological reagents are in contact with the surfaces of the unit across a high surface area (i.e. there is a high surface area:volume ratio) appears to magnify any incompatibilities of the reagents, to the extent that conventional PCR reaction conditions may fail to give a reaction.

The applicants have found that surprisingly PCR reactions can be successfully effected in units which have high surface area: volume ratios and are made of relatively simple, readily available components, and that metal substrates can be used under particular PCR conditions.

According to the present invention there is provided a method of carrying out an amplification reaction, said method comprising supplying to a well in a disposable unit (a) a sample which contains or is suspected of containing a target nucleic acid sequence (b) primers, nucleotides and enzymes required to effect said amplification reaction and (c) a buffer system, and subjecting the unit to thermal cycling conditions such that any target nucleic acid present within the sample is amplified; wherein the disposable unit comprises a thermally conducting layer and a facing layer having one or more reagent wells of up to 1000 microns in depth defined therebetween; and the reaction mixture comprises at least one of the following:

A) a buffer system wherein the p.H. is above 8.3;

B) a detergent; and/or

C) a blocking agent.

Target nucleic acids include DNA and RNA.

Suitable amplification reactions include the polymerase chain reaction as mentioned above. In this case, the primers used are amplification primers and the enzymes comprise nucleic acid polymerase, in particular thermally stable DNA polymerase such as TAQ polymerase.

Suitably the wells are from 100-1000 microns in depth and preferably less than 500 microns in depth. In particular wells are from 100-500 microns in depth. Depth in this context relates to the distance between the thermally conducting layer and the facing layer.

Preferably, at least a buffer system wherein the p.H. is above 8.3 is employed.

Suitable buffer systems which allow an amplification reaction to proceed will vary depending upon the particular nature of the materials used in the construction of the disposable units and the reaction taking place. Generally speaking, the buffers used in conventional PCR reactions have a pH of the order of 8.3 and comprise 10 mM Tris HCl solution. When these conditions have been used in the disposable units described above, it may not be possible to achieve a successful amplification reaction.

Buffers used in the method of the reaction are suitably at a higher pH than this. For example, the pH of the buffer is suitably from 8.5-9.2, more suitably from 8.7-9.0 and preferably at about pH 8.8 @ 25° C.

The applicants have found that buffers which are at higher concentrations than standard PCR buffers are preferred. Particularly suitable buffers for use in the amplification reaction of the invention comprise from 30-70 mMTris HCl and preferably about 50 mM Tris HCl pH 8.8 @ 25° C.

Other suitable components for the buffer solution include 1.5 mM MgCl.

Small amounts, for example from 0.01 to 0.1% v/v and preferably about 0.05% v/v, of detergents such as Tween™ or Triton™ may also be present.

A particular example of such a buffer system is one which comprises from 30-70 mMTris HCl pH 8.8 @ 25° C.

The presence of a blocking agent such as bovine serum albumin (BSA) has been found to be advantageous, in particular where the reagents undergoing reaction are directly in contact with the metal layer of the disposable unit.

Thereafter, amplification product can be detected for example, by removing the product from the well and separating it on an electrophoretic gel as is known in the art. Preferably however, reagents used in the amplification such as the primers are labelled with a fluorescent label, or a fluorescently labelled probe, able to hybridise to the target sequence under conditions that may be generated within the disposable unit.

Where the disposable unit comprises multiple wells, each may be pre-dosed with different PCR primers as well as the DNA polymerase enzyme. This gives the possibility that a single sample may be simultaneously tested for the presence of a range of different target sequences.

Suitably the metal used in the thermally conducting layer of the disposable unit is aluminium. The aluminium facing layer is suitably in the form of an aluminium foil. If required the foil may be coated with a plastic or other biocompatible layer but this is not required in order to effect a successful PCR reaction in accordance with the invention. A particularly suitable coating material is polystyrene or other material which allows the layer to be heat-sealed to the facing layer. This avoids the need for the presence of an adhesive. A particular example of heat-sealable polystyrene coated aluminium film is available from Advanced Biotechnologies, (Epsom UK), and is sold as Thermoseal AB-0598.

The facing layer may be thermally conducting or thermally insulating depending upon whether it is intended to supply heat to the unit at one or both faces. Where a thermally conducting layer is required, it is suitably an aluminium layer, preferably with heat sealable coating for example of polystyrene. This allows ready manufacture of the units by heat sealing two layers together. Areas are left unsealed so as to provide one or more reagent wells between the layers as well, as channels allowing reagent materials to be introduced into the wells.

In a preferred embodiment however, the facing layer is of a biocompatible plastics material such as polypropylene or polycarbonate, which is transparent. This allows the progress of reactions conducted in the wells to be monitored. For example, where the amplified reaction utilises visible label means, such as fluorescent labels, the progress of the reaction can be monitored using a fluorescence detection device as is well known in the art. Examples of suitable fluorescent assays are described for instance in International Patent Application No's PCT/GB98/03560, PCT/GB98/03563 and PCT/GB99/00504.

In a particularly preferred embodiment the unit used in the method has a composite structure comprising a spacing layer having holes and channels define the wells and channels adhered between the thermally conducting layer and the facing layer. Suitably the spacing layer is of a relatively rigid biocompatible plastics material such as polycarbonate. Where an adhesive is employed to secure the layers of the composite structure, the adhesive must itself be biocompatible. An example of such an adhesive is 7957 MP adhesive available from 3M. Where component layers of the composite structure are heat sealable, then this may provide a preferred form of assembling the unit as the requirement for further chemicals in the vicinity of the reagent is avoided.

Preferably the unit contains a plurality of reagent wells, for example from 10-100 reagent wells, and generally from 30-96 wells. This form allows a plurality of different reactions to be effected at the same time. Reagents may be introduced by way of one or more channels provided in the unit and open at the edge thereof.

Suitably the wells are each connected to a common reagent channel to allow ingress of sample into each well. Suitably the channel is of sufficient dimensions to prevent mixing of reagents in individual wells by convection, and furthermore to limit significant mixing as a result of diffusion effects. If required, each well can be sealable once filled, for example by mechanical deformation of one or both layers of the unit or by heat sealing.

If necessary or desired spacer means such as small glass balls (Ballotini balls) may be present within the wells in order to ensure they remain sufficiently open to allow easy ingress of reagents.

In general, certain reagents and in particular PCR reagent primers or probes, are introduced into the wells, suitably in dried form, prior to the construction of the unit. Thus the reagents are placed or printed onto one of either the thermally conducting layer or the facing layer before the layer is adhered to the other layer or to the spacing layer where present.

The disposable units are suitably of a convenient size. For example, they may be of "credit card" or "chip" dimensions or they may be similar in size to a microscope slide.

Thus the units will generally be of square or rectangular shape where each side is suitably from 5 to 25 cm long. The thickness of the unit will depend upon the nature of the particular layers used but they will generally be as thin as possible consistent with a mechanically robust structure as this will ensure that reagents are heated in as rapid and as even a manner as possible.

Generally however, the thermally conducting layer and any thermally conducting facing layer will be of the order of from 5-25 microns thick. Thermally insulating spacing layers may be thicker, for example from 100-500 microns thick. Spacing layers will be sufficiently thick to ensure that the well dimension is of the order of from 100-1000 microns, preferably from 100-500 microns. Other spacing means, such as Ballotini balls, where used, will be suitably dimensioned to ensure this level of distance between the conducting layer and the facing layer in the wells.

Preferably the opening into wells within the unit is by way of a common channel which has a single opening in order to simplify the filling operation and to minimise the risk of contamination. In order to fill such a unit with a liquid sample, air must be expelled. This may be done by means of a pump arrangement or by filling the unit in a vacuum chamber. The access channel of the unit is placed in contact with a liquid sample which will generally include PCR buffers, within a vacuum chamber. The chamber is first evacuated to eliminate air from the unit. Subsequent return to pressure forces liquid into the wells in the unit.

This arrangement of disposable unit forms a further aspect of the invention. Thus in a further embodiment, the invention provides a disposable unit for conducting a thermal cycling reaction, said unit comprising a thermally conducting layer and a facing layer having a plurality of reagent wells defined therebetween, characterised in that all the wells are fed by a common channel which includes a single opening to the outside of the unit.

Suitably such units may include some or all the other preferred features described above. In particular the wells are predosed with dried reagents, such as PCR reagent primers or probes. In addition thermally conducting layer is suitably a metal layer.

In a further embodiment, the invention provides a method of filling a disposable unit as described above with a liquid, said method comprising using air pressure to force the liquid into the unit. This may be effected by placing the unit and said liquid in a vacuum chamber, reducing pressure in said chamber such that gas is evacuated from the disposable unit, immersing at least the opening of said unit in said liquid, and increasing pressure in said chamber such that liquid is forced to enter the unit through the opening.

Preferably, the opening is immersed in said liquid before the pressure in the chamber is reduced.

Suitable vacuum chambers include vacuum ovens as are known in the art.

The disposable units described above can be used in a variety of apparatus adapted for thermal cycling reactions including that described in WO98/09728.

In a particularly preferred embodiment however, the method is effected in apparatus which comprises a plurality of heating blocks and conveyor means for holding and moving disposable units between the blocks. Suitably there are sufficient blocks to effect different stages of an amplification reaction. For example, a typical PCR reaction involves a cycling process of three basic steps.

Denaturation: A mixture containing the PCR reagents (including the nucleic acid to be copied, the individual nucleotide bases (A, T, G, C), suitable primers and polymerase enzyme) are heated to a predetermined temperature to separate the two strands of the target nucleic acid.

Annealing: The mixture is then cooled to another predetermined temperature and the primers locate their complementary sequences on the nucleic acid strands and bind to them.

Extension: The mixture is heated again to a further predetermined temperature. The polymerase enzyme (acting as a catalyst) joins the individual nucleotide bases to the end of the primer to form a new strand of nucleic acid which is complementary to the sequence of the target nucleic acid, the two strands being bound together.

Typical denaturation temperatures are of the order of 95° C., typical annealing temperatures are of the order of 55° C. and extension temperatures of 72° C. are generally of the correct order.

In a preferred apparatus for use in the method of the invention, at least two and preferably three heating blocks are provided, each of which is under the control of an automatic temperature control means. In use, one block is maintained at the denaturation temperature, one block is maintained at the annealing temperature and one block is maintained at the desired extension temperature. The disposable unit is then transferred sequentially between the blocks using the conveyor means, such as a conveyor belt, and held in the vicinity of each of the said blocks for a sufficient period of time to allow the unit to reach the temperature of the block and to allow the relevant stage of the amplification reaction to take place. The conveyor means suitably comprises a timing belt attached to a stepper motor.

Each heating block can be segregated such that individual wells or groups of wells within the disposable unit reach different temperatures in some or all of the reaction stages. For example, the annealing block could be segregated into four zones to allow four different annealing temperatures to be reached in different wells in the disposable unit. This may be required to ensure the specificity of four different specific amplification reactions.

If necessary, actuators such as solenoids, may be provided above each block and arranged to clamp the disposable unit against the block when it is arranged above it so as to ensure good thermal contact.

Suitably the actuators themselves may comprise heating elements, which are maintained at similar temperatures to the blocks. These can then contribute to the heating effect to ensure that the desired reaction temperature can be reached within the unit as rapidly as possible. This may be particularly useful where the facing layer of the disposable unit is a thermally conducting layer such as an aluminium layer.

Operation of the conveyor means, the heating blocks, the actuators and the heating elements are controlled automatically by a computer operating a suitable algorithm to effect the desired amplification reaction.

An alternative form of heating apparatus may comprise an electrically conducting polymer, which may be integral with or arranged in close proximity to the disposable unit. Such apparatus is described and claimed in PCT/GB97/03187.

In a particularly preferred embodiment, the apparatus used in the method further comprises means to detect the presence of labelled reagents within the disposable unit. This may comprise a fluorescence detector device as mentioned above. Where the facing layer of the disposable unit is of a transparent material, the fluorescence detector device can be used to detect signal generated within a well either at the end of or at any stage during the amplification reaction. Such a system may be particularly useful in connection with assays such as the TAQMAN™ assay, where continuous monitoring of the signal from a dual labelled probe during a PCR reaction provides the basis for quantitation of the target sequence.

The detector device is suitably arranged such that the conveyor means passes the disposable unit before it at the desired stage or stages during the amplification reaction.

Amplification reactions as described above are suitably carried out rapidly, for example in less than 20 minutes. This may be achieved by holding the reagents at the temperatures required for the various for about 30 seconds. This means that the results of the reaction can be ascertained early and also that the effects of diffusion of reagents between wells where there is a common channel are minimised or eliminated.

In a particular embodiment, the invention provides method of carrying out an amplification reaction, said method comprising supplying to a well in a disposable unit as described above (a) a sample which contains or is suspected of containing a target nucleic acid sequence (b) primers and enzymes required to effect said amplification reaction and (c) a buffer system which allows the amplification reaction to be carried out in said unit; subjecting the unit to thermal cycling conditions such that any target nucleic acid present within the sample is amplified.

Preferred variants including buffer systems, disposable units etc. are as set out above. In particular, said disposable unit comprises a thermally conducting layer and a facing layer having one or more reagent wells defined therebetween, characterised in that said thermally conducting layer comprises a metal.

BRIEF DESCRIPTION OF THE DRAWINGS

The invention will now be particularly described by way of example with reference to the accompanying diagrammatic drawings in which.

The following Example illustrates the invention.

Figure 1:
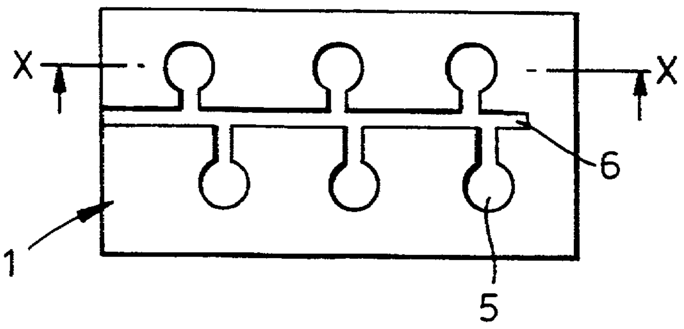
FIG. 1 shows an embodiment of a disposable unit useful in the method of the invention.
Figure 2:
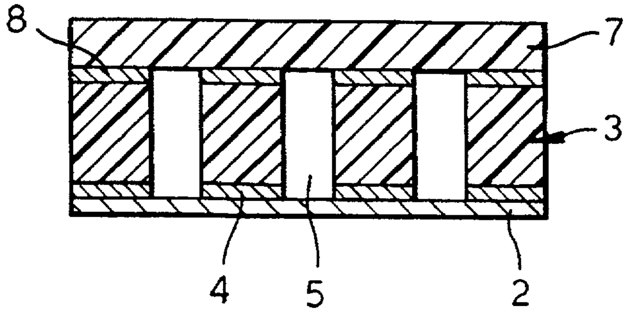
FIG. 2 is an expanded section on line X-X of FIG. 1.

The disposable unit 1 illustrated in FIG. 1 comprises a "credit card" size unit having a thin (approximately 10-20 μm) backing layer 2 of aluminium foil (FIG. 2). A spacing layer 3 of polycarbonate approximately 175-250μ thick is adhered to the backing layer 2 by means of an adhesive layer 4. Holes 5 and a channel 6 interconnected with the holes 5, is provided in the spacing layer 3. A facing layer 7, also of polycarbonate and of the order to 175 μm thick is adhered to the spacing layer 3 by a further adhesive layer 8.

Dried reagents (not shown) such as PCR reagents as described above may be applied to the backing layer 2 or the facing layer 7 prior to assembly by the adhesive layers. These reagents are applied such that they will be coincident with holes 5 spacing layer 3.

Once assembled, the holes 5 define reagent wells containing the pre-dried reagents.

Figure 3:
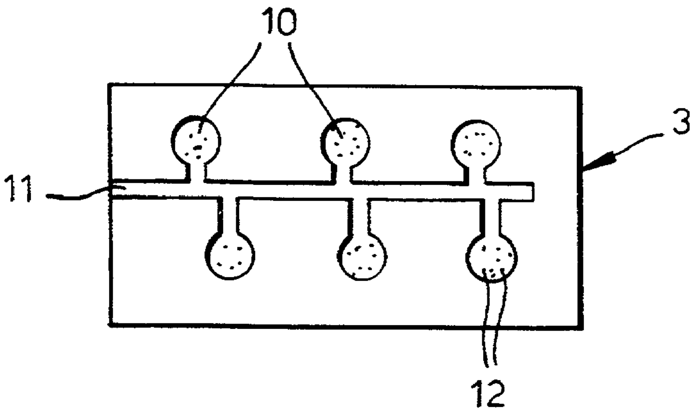
FIG. 3 shows an alternative embodiment of the disposable unit useful in the method of the invention.

In the embodiment of FIG. 3, both the backing layer 3 and the facing layer 7 comprise a heat sealable aluminium foil, in particular Thermoseal, which comprises a 20 μm thick aluminium layer coating with an approximately 5 μm thick polystyrene coating thereon. By selectively heat sealing the layers together, wells 10 and an interconnecting channel 11 can be defined.

Spacing within the wells is achieved in this instance by the presence of glass Ballotini balls 12, suitably ranging in size from 210 to 325 μm diameter.

Again, dried reagents such as PCR reagents appropriate for use in the method of the invention are suitably applied to either the backing layer 3 or the facing layer 7 prior to heat sealing, and arranged such that in the final unit, they are present within the wells 10.

Figure 4:
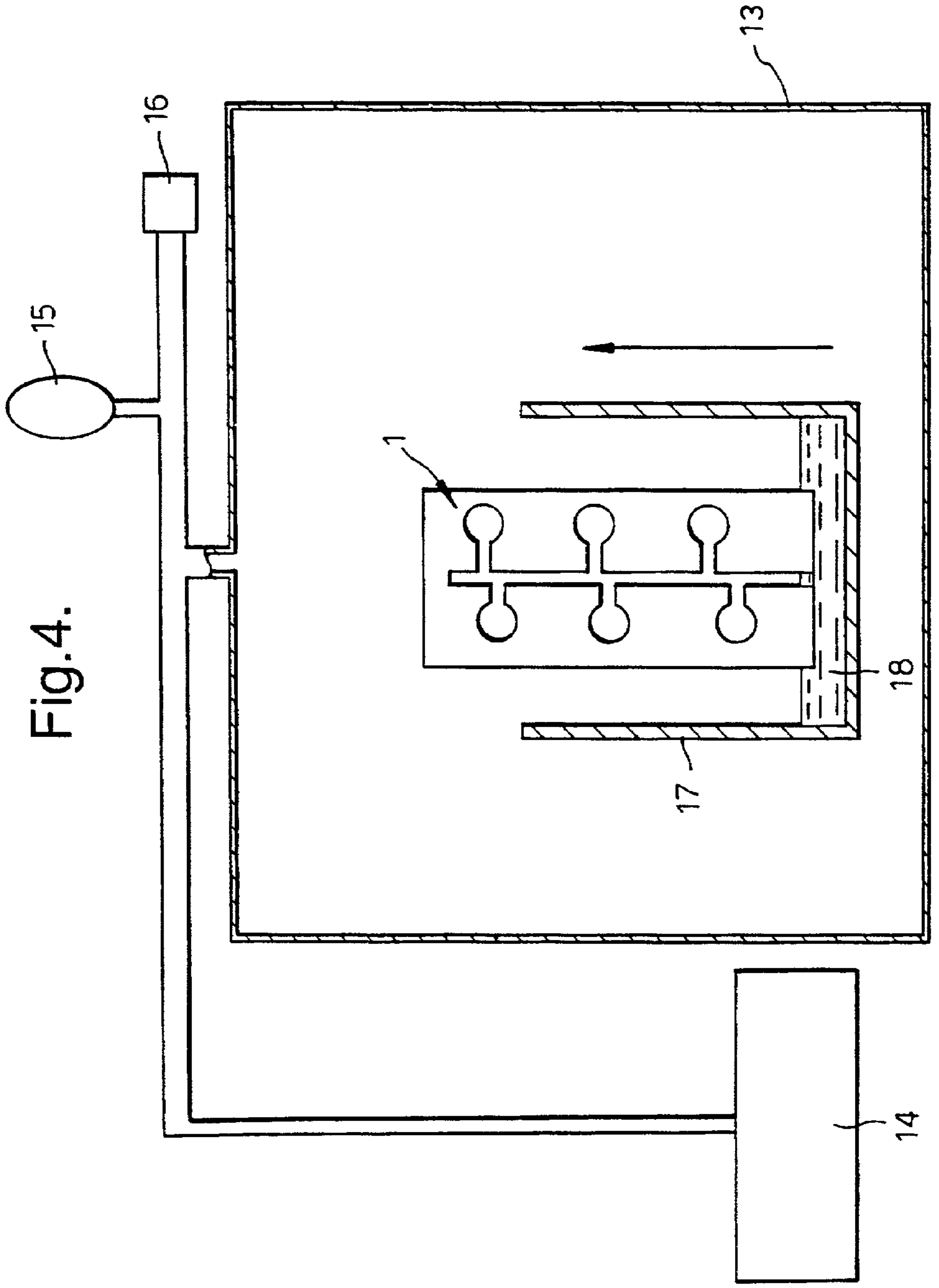
FIG. 4 is a schematic diagram of apparatus used to fill a disposable unit.

The arrangement illustrated in FIG. 4 shows one system for filling the units. This system comprises a vacuum oven 13 attached to a vacuum pump 14 which is controlled by a regulator 15. A regulator valve 16 is provided in the system so as to allow the system to be opened to atmosphere. A disposable unit 1, pre-dosed with dried PCR reagents, is placed in the oven within a container 17 and arranged such that the open end of the channel is in contact with a liquid 18 comprising the sample under test and buffers etc. required for the PCR reaction.

The vacuum pump 14 is then operated to evacuate the oven 13. Air in the wells 5 and channel 6 in the disposable unit 1 is bubbled through the liquid 18. Once the vacuum has been established, the pressure within the oven 13 is allowed to increase by operation of the valve 16, whereupon liquid 18 is forced into the channel 6 and wells 5 of the unit 1.

The filled unit is then removed from the oven and the open end of the channel 6 sealed for example by heat sealing if appropriate or by addition of an adhesive such as Araldite™.

This unit is then subjected to thermal cycling such that PCR amplification reactions take place in each well provided the sample includes nucleic acid which hybridises to the primers present in the well.

EXAMPLE 1

Materials used in this experiment were magnesium Chloride (Product No M-1028), Bovine Serum Albumin (Product No B-8667), Glycerol (Product No G-5516), Trizma® pre-set crystals pH 8.8 (Product No T-5753), Tween®20 (Product No P-2690), HPLC Mega ohm water (Product No 27,073-3) and Ammonium Sulphate (Product No 7783-20-2), obtained from Sigma Chemicals, Fancy Road, Poole, Dorset, UK. Tag DNA polymerase 5 units/μl, and PCR dNTP's nucleotides were obtained from Boehringer Mannheim UK (Diagnostics & Biochemicals) Limited, Bell Lane, Lewes, East Sussex BN7 1LG, UK). Custom oligonucleotide primers (HPLC Grade) were obtained from Cruachem Ltd, Todd Campus, West of Scotland Science Park, Acre Road, Glasgow G20 OUA, UK.

The target DNA was an engineered internal control construct, pYP100ML, containing PCR primer sites for the anticoagulase gene of *Yersinia pestis*. The primer sequences were YPPA155 (dATGACGCAGAAACAGGAAGAAAGATCAGCC) and YPP229R (dGGTCAGAAATGAGTATGGATCCCAGGATAT). These primers amplify a 104 bp amplicon.

Reagents were prepared using the formulations in Tables 1. The buffers had four different adjuncts added, resulting in 16 buffer formulations (Table 2).

PCR was performed with one of the buffer combinations, 200 μM dNTP's (each), 1 μM primers, and 0.04 U/μl Taq DNA polymerase. 10 pg/μl of pYP100ML construct was used as DNA template.

The apparatus for filling the disposable units consisted of an Edwards Speedvac II pump connected to a vacuum oven.

PCR reagents (~250 μl volume) were loaded into the groove of the filling tool and the disposable unit set in place. The unit and filling tool were placed into a vacuum oven and a vacuum was drawn. The pump was operated in accordance with the manufacturer's instructions. Once a vacuum of ~20 mbar was reached, the pump was switched off. Once the pressure was equilibrated at atmospheric pressure, the disposable unit assembly was removed. The channels in the disposable units contained the PCR reagents. The opening of the credit card was sealed with a PCR compatible adhesive (Araldite®) was allowed to cure on ice for ~1 hr.

Testing of the disposable units was carried out on the Perkin Elmer 9700 machine using the following temperature profile: denature at 97° C. for 20 seconds, annealing at 50° C. for 20 seconds, and extension at 75° C. for 20 seconds. The 9700 block was flooded with oil to ensure good thermal contact between the block and credit card. Control PCR reaction mixtures were also run on this machine using the above parameters.

Testing was also carried out on a prototype Thermal Cycling Instrument using the following reaction parameters: denature at 98° C. for 10 seconds, annealing at 50° C. for 10 seconds, and extension at 77° C. for 10 seconds.

Positive and negative (no template) controls were performed in MicroAmp® reaction vessels and thermocycled in the Perkin Elmer 9700 PCR instrument.

The sample was carefully extracted from the credit card by means of a pipette tip and analysed by conventional agarose gel electrophoresis for signs of successful DNA amplification. The PCR products were run on a 2% (w/v) agarose in 1×T.A.E. buffer. Ethidium bromide was added to the gel at a final concentration of 0.5 μg/ml. Electrophoresis was performed in 1×T.A.E. buffer and allowed to run for ~30-40 minutes at 100 volts. Following electrophoresis, bands on the gel were visualised using ultraviolet light and images recorded using a Bio/Gene gel documentation system.

The YPPA155/YPP229R primer pair and pYP100ML construct was used to study the biocompatibilty of two types of disposable unit as a platform for PCR.

The first was a unit where both the thermally conducting layer and the facing layer were of Thermo-seal aluminium which had been heat sealed together and contained Ballotini balls as spacers. The second unit was a composite unit, comprising an aluminium foil layer as the thermally conducting layer, a transparent polycarbonate layer as the facing layer and a polycarbonate spacing layer (175 μm thick). Layers were adhered together using 7957 MP adhesive.

The units were evaluated for PCR compatibility as well as structural integrity and retention of volume during thermal cycling.

All the chemistry PCR formulations were tested on a block thermal cycler in a tube PCR and were shown to be effective when analysed using the technique of agarose gel electrophoresis.

Work then commenced on testing the PCR formulations in the disposable units of the invention. The compositions which gave positive results are indicated in Table 3 hereinafter.

Particularly rapid PCR reactions of approximately 19 minutes were achieved using apparatus of the invention comprising 3 heating blocks as described above.

The study demonstrated the using the disposable units of the invention as a PCR platform.

TABLE 1

Buffer Composition.
Final 1X composition

| Buffer | Composition |
|---|---|
| 1 | 50 mM Tris.HCl pH 8.8<br>1.5 mM $MgCl_2$ |
| 2 | 50 mM Tris.HCl pH 8.8<br>1.5 mM $MgCl_2$<br>20 mM $(NH_4)_2SO_4$ |
| 3 | 75 mM Tris.HCl pH 8.8<br>1.5 mM $MgCl_2$ |
| 4 | 75 mM Tris.HCl pH 8.8<br>1.5 mM $MgCl_2$<br>20 mM $(NH_4)_2SO_4$ |

TABLE 2

Adjuncts added to Buffers.
Final 1X composition

| | Adjuncts |
|---|---|
| A | 0.05% (v/v) TWEEN + 250 ng/µl BSA |
| B | 0.05% (v/v) TWEEN |
| C | 8% (v/v) Glycerol + 250 ng/µl BSA |
| D | Native (No adjuncts added) |

TABLE 3

A summary of the results obtained on the affect of using disposable units of the invention as a platform for PCR

| Disposable unit | Materials exposed to PCR solution | Successful chemistry composition |
|---|---|---|
| Thermo-seal aluminium | Polycarbonate, Polystyrene, Glass | Buffer 1 Adjunct B<br>Buffer 1 Adjunct A<br>Buffer 1 Adjunct B<br>Buffer 2 Adjunct A<br>Buffer 4 Adjunct A<br>Buffer 4 Adjunct B |
| Composite | Polycarbonate, Aluminium, 7957 MP Adhesive | Buffer 2 Adjunct A |

EXAMPLE 2

A range of materials including aluminium and Thermo-seal foil AB0598 with a polystyrene coating were tested for possible use in the development of a disposable unit for PCR. These were tested under normal PCR conditions and in the presence of a blocking agent (BSA) to determine their compatibility with the reaction.

About 25 pieces, 5 mm×5 mm square (approx), of each material were cut from sheets supplied. These were put into 1.5 ml Eppendorf tubes with 1 ml 10% Tween 20 in deionised water. The tubes were vortexed and placed at 70° C. for 1-2 hours.

The pieces were recovered by filtration through 1 layer of blue roll, placed in about 10 ml deionised water in a 25 ml sample bottle and shaken. This filtration and wash step was done 3 times.

Pieces of material were then placed in 1.5 ml Eppendorf tubes and stored, refrigerated, until used in a PCR reaction.

Washed samples of the materials were placed in Perkin Elmer PCR reaction tubes with various PCR mix as follows:

PCR Reagents 10 mM Tris.HCl pH 8.3

50 mM KCl 2 mM or 5 mM $MgCl_2$ 0.2 mM each dNTP

1 µM each primer 1.25 u Taq DNA polymerase 0 or 0.025% Bovine Serum Albumen (BSA)

0 or 0.5 ng *E. coli* DNA

In a volume of 50 µl.

The primers used delineate a 663 base section of the *E. coli* Aro A gene. The left primer is a 22mer and the right one a 21mer. The PCR thermal cycle was:

94° C.×5 min (94° C.×30 s, 55° C.×30 s, 72° C.×1 min)$_{30}$72° C.×7 min, 4° C. hold.

Either 1 or 2 pieces of each material were added to the reaction. Control reactions without test material and without DNA template were run each day. Amplicon was detected as bands on a gel. The results are summarised in Table 4.

TABLE 4

| | PCR Mix | | | |
|---|---|---|---|---|
| Material | 2 mM $MgCl_2$ | 5 mM $MgCl_2$ | 2 mM $MgCl_2$ + BSA | 5 mM $MgCl_2$ + BSA |
| 1 piece Aluminium foil (unwashed) | − | − | + | + |
| 1 piece Aluminium foil (washed in Tween) | − | − | ++ | ++ |
| 1 piece Thermo-seal foil AB-0598 | − | − | ++ | ++ |
| 2 pieces Aluminium foil (unwashed) | − | − | + | + |
| 2 pieces Aluminium foil (washed in Tween) | − | − | + | ++ |
| 2 pieces Thermo-seal foil AB-0598 | − | − | − | ++ |

where
− indicates that no band was seen
+ indicates the presence of a band
++ indicates the presence of a brighter band.

The results show that BSA increased the compatibility of the aluminium based materials (as well as many others—results not shown).

The invention claimed is:

1. A method of carrying out an amplification reaction, said method comprising supplying to a reagent well in a disposable unit, a reaction mixture comprising: (a) a sample which contains or is suspected of containing a target nucleic acid sequence; (b) primers, nucleotides and enzymes required to effect said amplification reaction; and (c) a buffer system, wherein the pH of said buffer system is from 8.7-9.0, and subjecting the disposable unit to thermal cycling conditions such that any target nucleic acid present within the sample is amplified; wherein the disposable unit comprises a thermally conducting layer and a facing layer having one or more reagent wells up to 1000 microns in depth defined therebetween, and wherein said reaction mixture further comprises a detergent and/or a blocking agent.

2. A method of carrying out an amplification reaction, said method comprising supplying to a reagent well in a disposable unit, a reaction mixture comprising: (a) a sample which contains or is suspected of containing a target nucleic acid sequence; (b) primers, nucleotides and enzymes required to effect said amplification reaction; and (c) a buffer system, wherein the pH of said buffer system is at or above [1]8.8, and subjecting the disposable unit to thermal cycling conditions such that any target nucleic acid present within the sample is amplified; wherein the disposable unit comprises a thermally conducting layer and a facing layer having one or more reagent wells up to 1000 microns in depth defined therebetween, and wherein said reaction mixture further comprises a detergent and/or a blocking agent.

3. The method according to claim 1 or 2, wherein the buffer system comprises from 30-70 mM Tris HCl.

4. The method according to claim 3, wherein the buffer system comprises about 50 mM Tris HCl, pH 8.8 at 25° C.

5. The method according to claim 1 wherein the reaction mixture further comprises from 0.01 to 0.1% v/v detergents.

6. The method according to claim 1 wherein the reaction is effected in the presence of a blocking agent which comprises bovine serum albumin (BSA).

7. The method according to claim 1 wherein the thermally conducting layer of the disposable unit is metal.

8. The method according to claim 7 wherein the thermally conducting metal layer of the disposable unit is aluminum.

9. The method according to claim 7 wherein the thermally conducting metal layer is coated with a plastic or other biocompatible layer.

10. The method according to claim 9 wherein the biocompatible layer is polystyrene.

11. The method according to claim 1 wherein the thermally conducting layer and the facing layer of the disposable unit are heat-sealed together.

12. The method according to claim 1 wherein the facing layer of the disposable unit comprises a thermally conducting layer.

13. The method according to claim 1 wherein the facing layer of the disposable unit is of a transparent biocompatible plastics material.

14. The method according to claim 1, wherein the disposable unit further comprises a spacing layer having holes and channels to define reagent wells and channels adhered between the thermally conducting layer and the facing layer.

15. The method according to claim 14 wherein the layers are adhered together by means of a biocompatible adhesive and the reaction is effected in the presence of a blocking agent which comprises bovine serum albumin.

16. The method according to claim 1 wherein spacer means are provided within each reagent well.

17. The method according to claim 1 wherein the reagent wells are pre-dosed with dried reagents.

18. The method according to claim 17 wherein the dried reagents are PCR reagent primers or probes.

19. The method according to claim 1 wherein the disposable unit contains a plurality of reagent wells and each reagent well is fed by a common channel which has a single opening to the outside of the unit.

20. The method according to claim 1 wherein the disposable unit is placed in apparatus comprising at least two heating blocks, each of which is under the control of an automatic temperature control means, and conveyor means for holding and transferring a disposable unit sequentially between the blocks.

21. The method according to claim 20 wherein the apparatus further comprises an actuator above each block and arranged to clamp the disposable unit against the respective block.

22. The method according to claim 20 wherein the at least one of the heating blocks is segregated and each segment is held at a different temperature.

23. The method according to claim 1 wherein the disposable unit is integral with or arranged in close proximity to an electrically conducting polymer.

24. The method according to claim 1 wherein the presence of labelled reagents within the disposable unit is monitored.

25. A method of filling a disposable unit for conducting thermal cycling reactions with a liquid, comprising:

using air pressure to force liquid into the disposable unit; wherein the disposable unit for conducting thermal cycling reactions comprises a thermally conducting layer and a facing layer having a plurality of reagent wells defined therebetween; wherein all the reagent wells are fed by a common channel which includes a single opening to the outside of the disposable unit;

and wherein the method comprises placing the disposable unit and said liquid in a vacuum chamber, reducing pressure in said vacuum chamber such that air is evacuated from the disposable unit, immersing at least the single opening of said unit in said liquid, and increasing pressure in said vacuum chamber such that liquid is forced to enter the disposable unit through the single opening.

26. The method according to claim 25 wherein the single opening is immersed in said liquid before the pressure in the vacuum chamber is reduced.

* * * * *

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Synthetic primer

<400> SEQUENCE: 1
atgacgcaga aacaggaaga aagatcagcc 30

<210> SEQ ID NO 2
<211> LENGTH: 30
<212> TYPE: DNA
<213> ORGANISM: Artificial Sequence
<220> FEATURE:
<223> OTHER INFORMATION: Synthetic primer

<400> SEQUENCE: 2
ggtcagaaat gagtatggat cccaggatat 30